(12) United States Patent
Rathjen

(10) Patent No.: US 9,060,848 B2
(45) Date of Patent: *Jun. 23, 2015

(54) OPHTHALMOLOGICAL APPARATUS FOR BREAKDOWN OF EYE TISSUE

(71) Applicant: Ziemer Holding AG, Port (CH)

(72) Inventor: Christian Rathjen, Bremen (DE)

(73) Assignee: ZIEMER HOLDING AG (CH)

( * ) Notice: Subject to any disclaimer, the term of this patent is extended or adjusted under 35 U.S.C. 154(b) by 247 days.

This patent is subject to a terminal disclaimer.

(21) Appl. No.: 13/659,321

(22) Filed: Oct. 24, 2012

(65) Prior Publication Data
US 2013/0085483 A1 Apr. 4, 2013

Related U.S. Application Data

(63) Continuation-in-part of application No. 12/526,732, filed as application No. PCT/CH2007/000078 on Feb. 14, 2007, now Pat. No. 8,771,262.

(51) Int. Cl.
*A61B 18/18* (2006.01)
*A61F 9/009* (2006.01)
*A61F 9/008* (2006.01)

(52) U.S. Cl.
CPC .............. *A61F 9/009* (2013.01); *A61F 9/00825* (2013.01); *A61F 2009/00897* (2013.01)

(58) Field of Classification Search
CPC ................ A61F 9/009; A61F 9/00825; A61F 2009/00897; A61B 18/18
USPC ........... 351/200, 205, 206, 219, 246; 606/4–6
See application file for complete search history.

(56) References Cited

U.S. PATENT DOCUMENTS

2004/0254568 A1* 12/2004 Rathjen .............................. 606/4

FOREIGN PATENT DOCUMENTS

| EP | 1486185 A | 12/2004 |
|---|---|---|
| EP | 1731120 A | 12/2006 |
| JP | 2005152505 | 6/2005 |
| JP | 2006181358 | 7/2006 |
| JP | 2006341103 | 12/2006 |
| WO | WO 8906519 A | 7/1989 |

OTHER PUBLICATIONS

International Search Report dated May 7, 2007, issued in corresponding international application No. PCT/CH2007/000078.

* cited by examiner

*Primary Examiner* — James Greece
(74) *Attorney, Agent, or Firm* — Ostrolenk Faber LLP

(57) ABSTRACT

An ophthalmological apparatus (1) for breakdown of eye tissue includes a base station (2) with a light source (21) for generating light pulses and a support arm (3), with an application head (4) that can be placed onto an eye (6) mounted on the base station (2). The light pulses are transmitted from the base station (2) to the application head (4) through an optical transmission system (22). The application head (4) has a light projector (41) for focused projection of the light pulses for punctiform breakdown of eye tissue. The support arm (3) is of rigid design and, at one end, has a hinge ($R_z$) with a horizontally oriented rotation axis ($r_z$), the hinge ($R_z$) being mounted in such a way that the application head (4) can be placed onto the eye (6) with a rotation ($z_{rot}$) extending about the rotation axis ($r_z$).

13 Claims, 4 Drawing Sheets

OPHTHALMOLOGICAL APPARATUS FOR BREAKDOWN OF EYE TISSUE

CROSS-REFERENCE TO RELATED APPLICATION

This patent application is a continuation in part of U.S. patent application Ser. No. 12/526,732, filed Aug. 11, 2009, entitled "OPHTHALMOLOGICAL APPARATUS FOR BREAKDOWN OF EYE TISSUE," which is a 35 U.S.C. §371 National phase conversion of PCT/CH2007/000078, filed Feb. 14, 2007, the entire contents of each which are hereby incorporated by reference herein.

BACKGROUND

1. Field of the Disclosure

The present invention relates to an ophthalmological apparatus for breakdown of eye tissue. The invention relates in particular to an ophthalmological apparatus that comprises a base station with a light source for generating light pulses, an application head that can be mounted on the base station by means of a support arm and can be placed onto the eye, with a light projector for focused projection of the light pulses, and an optical transmission system for transmitting the light pulses from the base station through the support arm to the application head.

2. Related Art

Instances of ametropia such as myopia (short-sightedness), hyperopia (long-sightedness or far-sightedness) or astigmatism can nowadays be permanently corrected by refractive surgical treatment. Refractive surgical treatments are surgical operations on the eye which change the optical refractive power of the eye with the aim of bringing it as close to a desired value as possible. One of the most important methods in refractive surgery is so-called laser-assisted in situ keratomileusis (LASIK) in which the interior of the cornea is removed with the aid of a computer-controlled excimer laser after a corneal flap has previously been partially severed and folded aside. To produce the corneal flap, use is made of mechanical microkeratomes in which a driven scalpel cuts the corneal flap. Recently, such corneal flaps have also been cut with the aid of strongly focused femtosecond laser pulses, which have pulse widths of typically 100 fs to 1000 fs (1 fs=$10^{-15}$s). In addition to LASIK, there are further procedures for refractive correction that are performed on the cornea with the aid of femtosecond lasers.

Such a system is marketed, for example, by IntraLase Corp, in Irvine, Calif., USA under the name of Pulsion FS Laser. In this system, a light source (femto laser) is located in a base station and is connected to an optical application head via an articulated mirror arm. In addition to the optical transmission system, a deflection system (scanner) and the light projector, the application head also comprises viewing means, such as camera or surgical microscope, and therefore has a considerable weight of several kilograms. For orienting and applying the light projector onto an eye of a patient, the entire application head is moved via translatory drives. The patient lies on a bed and does not move. For reasons of weight, the application cannot be done by hand, and motorized drives are necessary. To avoid applying excessive forces to the patient, the laser system comprises force-measuring systems in the vertical application direction.

Systems for cutting the corneal flap with focused femtosecond laser pulses are also marketed by Zeiss Meditec AG, with its Visumax, and by 20/10 Perfect Vision Optische Geräte GmbH, with its Femtec. In these systems, the light projector is connected fixedly to the base station. In these systems, the patient is oriented in the horizontal plane and also vertically with respect to the light projector with the aid of a patient bed. Therefore, these systems too cannot be applied manually onto the patient's eye. In addition, the special patient bed has to be integrated into the safety system of the laser system in order to avoid uncontrolled movements of the bed. The bed is thus part of the laser system and thus increases the system costs and the space required. A suitable choice of bed by the person using the system is not possible.

In the aforementioned systems, the docking of the light projector onto the patient's eye is first effected by orientation in the horizontal plane in the x-direction and y-direction (centring of the eye) and then by lowering in the vertical z-direction.

EP 1731120 describes a system in which the application head is mounted flexibly on the base station via an articulated mirror arm composed of several arm elements and joints and permits manual application of the application head and light projector onto the eye of a patient. To permit the weight of the application head for manual application by means of the articulated mirror arm, the light projector has smaller lens systems compared to the previously known systems. In order to ensure that, despite the lens system of smaller dimensions, it is possible to work with focused laser pulses across an extensive work area on the eye, the application head additionally has movement drivers for moving the light projector in an advance direction and in a first scanning direction. An optical deflection to a vertical scanning direction is not possible, however. The limited work area permits only rapid positioning of the laser pulses within the work area. Limits are thus set on flexible positioning of the laser pulses across the entire eye.

SUMMARY

It is an object of the present invention to propose a novel ophthalmological apparatus for breakdown of eye tissue, which apparatus avoids at least some disadvantages of the prior art. A particular object of the present invention is to make available an ophthalmological apparatus for breakdown of eye tissue which enables manual application of the light projector onto an eye of a patient but permits a light projector with optics of high numerical aperture, which permits the focused projection of laser pulses in the whole viewable eye area both in the horizontal and also the vertical direction.

According to present invention, these objects are achieved in particular by the elements of the independent claims. Further advantageous embodiments are also set forth in the dependent claims and the description.

The ophthalmological apparatus comprises a base station with a light source for generating light pulses, a support arm mounted on the base station, an application head that is mounted on the support arm and can be placed onto an eye and has a light projector for focused projection of the light pulses for punctiform breakdown of eye tissue, and an optical transmission system for transmitting the light pulses from the base station through the support arm to the application head.

The aforementioned objects are achieved in the present invention particularly by virtue of the fact that the support arm is of rigid design and, at one end, has a hinge with a horizontally oriented rotation axis, the hinge being mounted in such a way that the application head can be placed onto the eye with a rotation (rotation movement) extending about the rotation axis. The rigid support arm, i.e. designed in one piece and inherently immovable, permits a stable and simple connection of the application head to the base station. In particular, the rigid support arm makes it possible to design the optical transmission system more simply than is the case, for example, with a multi-part articulated mirror arm. The hinge arranged horizontally on an end of the rigid support arm permits application of the application head or of the light projector onto the eye in the vertical direction via a preferably mechanically executed rotation movement, wherein the application head is guided on a kinematically generated arc, which permits a vertical movement component for placement onto the eye. The advantage of the rotation movement is its simple configuration and minimal mechanical friction. The support arm and the hinge thus permit controlled manual docking, i.e. application of the application head or light projector onto the eye, the user advantageously being able to employ his tactile senses in order to control the force or movement exerted via the tactile force and movement feedback. Because active systems for applying force and limiting force are unnecessary, increased safety is achieved only through the use of passive system elements. On account of the simply designed support arm and the actuators and sensors required only in small numbers, or not at all, a further simplified configuration and therefore lower costs are achieved. Moreover, the overall size of the components located directly over the patient can be reduced.

The hinge is preferably arranged on that end of the support arm directed away from the base station, and the application head is connected movably to the support arm via the hinge. By means of the movable arrangement of the application head on the rigid support arm via a hinge, the size and weight of the system part to be applied manually is reduced, which further facilitates the manual application and makes it controllable.

In an embodiment variant, the application head is connected fixedly to the support arm and the hinge is arranged on that end of the support arm directed towards the base station, such that the support arm and therefore the application head secured thereon is connected movably to the base station via the hinge. The advantage of a lengthened rotation arm is that the rotation executed during the application has a greater radius and therefore requires a smaller rotation angle for the vertical excursion, which once again means smaller deviations from a vertical application axis.

In another embodiment variant, the apparatus comprises positioning means for rotary and/or translatory movement of the support arm parallel to a positioning plane for the positioning of the application head over the eye. The positioning means comprise, for example, guide rails and/or drive means for translatory movements in a horizontal positioning plane and/or hinges that permit a rotation (rotation movement) about a vertically extending rotation axis.

In an embodiment variant, the apparatus comprises beam-deflecting means arranged in the support arm and used for deflecting the light pulses in at least two scanning directions, and the light projector is dimensioned such that, without mechanical movement of the light projector, deflected light pulses can be projected in a focused manner across an entire working area of preferably 11 mm in diameter for breakdown of eye tissue.

In another embodiment variant, the application head has a viewing window permitting a top view of the eye in the projection direction of the light projector. The viewing window permits a top view of the eye by way of optical viewing or measuring modules, e.g. cameras, microscopes, measuring devices, which are connected movably to the base station and which, oriented in the projection direction of the light projector, can be swivelled over the viewing window, while the application head is placed on or is being placed onto the eye. Moreover, the optical viewing or measuring modules can be swivelled away when not required. The possibility of optical viewing or measuring modules being able to be swivelled into and out of the line of sight above the eye means that the overall size and therefore the weight of the application head can be further reduced and its handling improved.

In an embodiment variant, weight compensation means are connected to the application head, in order to partially balance out the application head above the rotation axis in such a way that the application head can be placed onto the eye with an application force reduced by the inherent weight of the application head. By means of the only partially balanced out configuration of the masses involved in the rotation movement (application head and, depending on the design, the support arm), the application force on the eye can be generated by gravity.

In another embodiment variant, the light projector comprises a first lens system in a projection part of the application head oriented in the projection direction, and the light projector comprises a second lens system in a feed part of the application head angled away from the projection part and directed towards the support arm, said first and second lens systems being coupled via a deflecting mirror. The arrangement of the lens systems divided up into the projection part and feed part permits a reduction of the structural height of the light projector and thus of the application head. Moreover, external aids such as microscopes or measuring devices can be adapted more easily.

In an embodiment variant, the application head comprises a projection part oriented in the projection direction and a feed part angled away from the projection part and directed towards the support arm. The projection part is connected rotatably to the feed part, e.g. axially about a longitudinal axis extending through the feed part and/or about a transverse axis extending perpendicular to the longitudinal axis of the feed part. The rotatable connection of the projection part to the feed part allows light projector and securing means mounted thereon to be oriented precisely with the eye.

In another embodiment variant, the apparatus comprises a lock for fixing or releasing a rotation position of the application head about the rotation axis.

In one embodiment variant, the apparatus comprises height-defining means for determining a vertical position of the eye, and the base station comprises height-positioning means for setting a vertical basic position of the support arm. By setting a vertical basic position of the support arm, the rotation movement needed for vertical placement of the application head onto the eye can be reduced and thus be kept in an area closer to the vertical movement component, which on the one hand reduces the movement stroke necessary for the docking of the application head and on the other hand facilitates the horizontal orientation of application head and eye (centring).

In other embodiment variants, the application head has one or more grips and grip structures for manual handling, a contact body which can be placed onto the eye, is transparent at least in parts and is configured and arranged such that it sets a contacted area of the eye equidistant to a working surface, and securing means for fixing the application head on the eye by underpressure. The light source preferably comprises a femtosecond laser.

BRIEF DESCRIPTION OF THE DRAWINGS

An embodiment of the present invention is described below by way of example. The illustrative embodiment is depicted in the attached figures, in which.

DETAILED DESCRIPTION OF THE EMBODIMENTS

Figure 1:
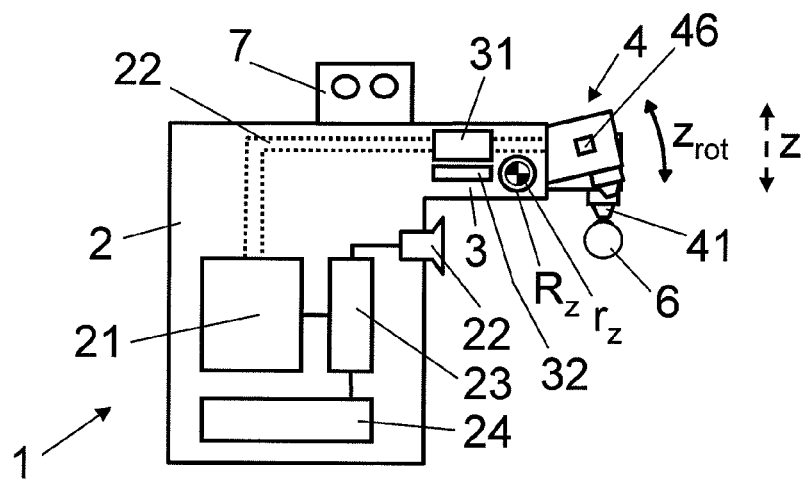
FIG. 1 shows a schematic side view of the ophthalmological apparatus, comprising a one-piece design of a base station with a support arm on which an application head is mounted rotatably.

In FIGS. 1 to 6, reference number 1 designates an ophthalmological apparatus for breakdown of eye tissue. The ophthalmological apparatus 1 comprises a base station 2 and an inherently rigid support arm 3 mounted thereon. An application head 4 is mounted on the support arm 3 fixedly or via a horizontally oriented hinge $R_z$. FIG. 1 also shows an optional optical viewing, imaging and/or measuring module 7 connected fixedly to the support arm 3, for example a monitor and/or a microscope for observing the application procedure (docking) and the treatment. In the embodiment variants according to FIGS. 1 to 6, the application head 4 is connected to the support arm 3 via the hinge $R_z$ so as to rotate about the horizontal rotation axis $r_z$. The hinge $R_z$ is in each case arranged at that end of the support arm 3 directed away from the connection of the support arm 3 to the base station 2. As is shown schematically in the side views in FIGS. 1 and 2, the hinge $R_z$ is arranged and configured such that, by the rotation $z_{rot}$ of the application head 4 about the rotation axis $r_z$, a vertical movement component can be executed in the z-direction for lowering and placing the application head 4 onto an eye 6. For manual handling, grips and/or grip structures 46 are mounted on the application head 4. In order to keep the mass inertia low, and to reduce the number of the moved components, the rotation axis $r_z$ is arranged close to the patient. A person skilled in the art will understand that the rotation of the application head 4 about the rotation axis $r_z$ can also be effected by means of a parallelogram guide, for example, with further hinges $R_z$ being used for this purpose.

Although this is only shown schematically in FIG. 1, the ophthalmological apparatus 1 in each case comprises a light source 21 (laser source) which is arranged in the base station 2 and generates light pulses, in particular a femtosecond laser for generating femtosecond laser pulses, and an optical transmission system 22 for transmitting the light pulses from the base station 2 through the support arm 3 to the application head 4. The ophthalmological apparatus 1 preferably also comprises a lock 32 for fixing or releasing a position of rotation of the application head 4 about the rotation axis $r_z$, for example a friction coupling.

Beam-deflecting means 31 are inserted into the optical transmission system 22 and are designed to deflect the light pulses in at least two scanning directions. A scanner suitable for the beam-deflecting means 31 is described in EP 1731120, for example. Galvanoscanners or acousto-optic modulators are also suitable. The beam-deflecting means 31 are preferably arranged in the support arm 3 in order to minimize the distance to the application head 4. The application head 4 comprises a light projector 41 with a lens system 42, 43 for focused projection of the light pulses into and/or onto the eye 6, in order to effect a punctiform breakdown of the eye tissue. The deflected light pulses are transmitted onwards by the optical transmission system 22 via the beam-deflecting means 31 to the light projector 41. The beam-deflecting means 31 and the light projector 41 are designed to scan a contiguous work area extending across the entire viewable region of the eye and to work with a focusing effect such that contiguous sections in the eye tissue, in particular in the cornea, can be cut. The beam-deflecting means 31 and the light projector 41 not only permit focused scanning of a plane work region, for example a horizontal work region, but, by targeted vertical positioning of the focus, also three-dimensionally defined work regions, for example vertical and curved sectional surfaces.

Although this is not shown in the figures, it should be noted that the application head 4 comprises a contact body which can be placed onto the eye 6, is transparent to light at least in parts and is configured and arranged such that it sets a contacted area of the eye 6 preferably equidistant to a work surface, and has securing means for fixing the application head 4 to the eye 6 by underpressure. Contact bodies can be plane or spherical, for example.

Figure 5:
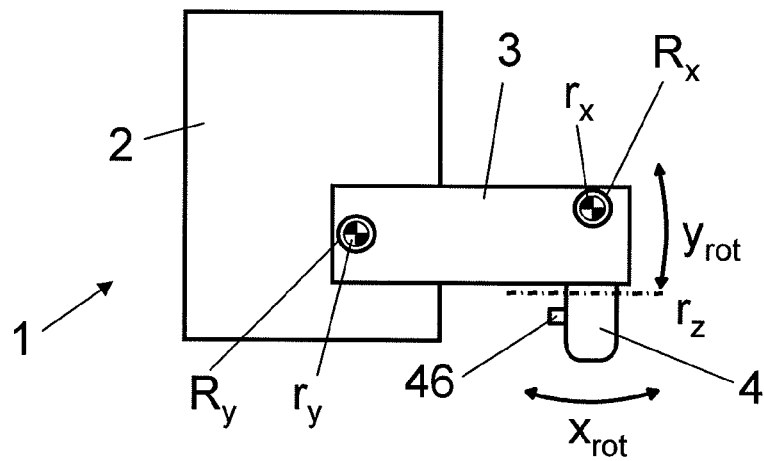
FIG. 5 shows a schematic top view of an ophthalmological apparatus comprising a support arm which can be moved in rotation relative to the base station about two vertical axes of rotation in the positioning plane and on which the application head is mounted rotatably.
Figure 6:
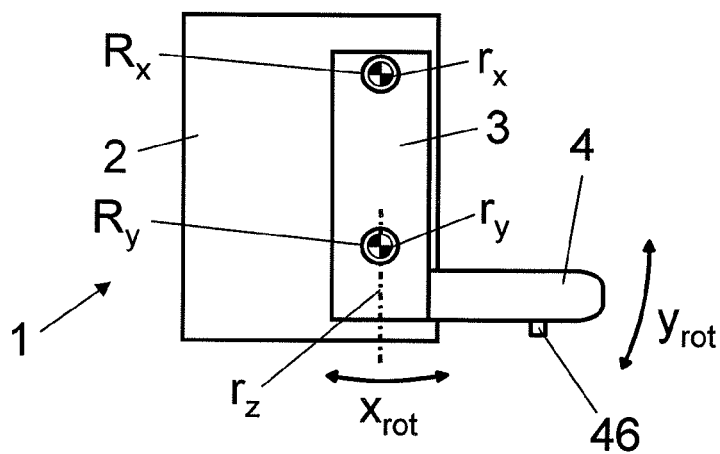
FIG. 6 shows a schematic top view of another ophthalmological apparatus comprising a support arm which can be moved in rotation relative to the base station in the positioning plane about two vertical axes of rotation and on which the application head is mounted rotatably.
Figure 7:
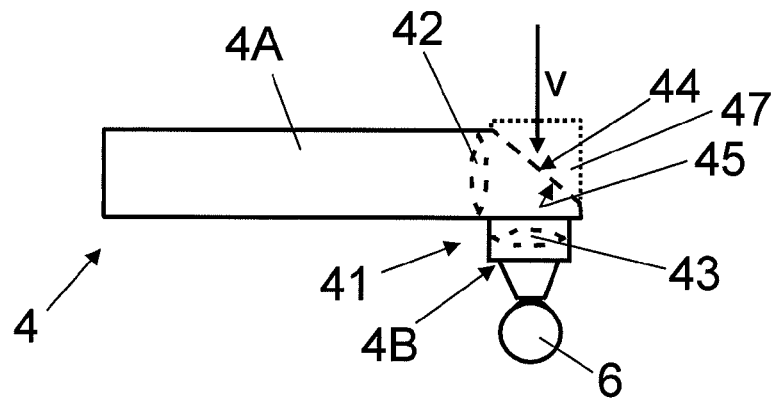
FIG. 7 shows a schematic side view of the application head, which comprises one lens system in a feed part to the support arm and another lens system in an angled projection part.

As is shown schematically in FIG. 7, the application head 4, in an embodiment variant that can be combined with FIGS. 1-6, has a feed part 4A connected to the support arm 3, and a projection part 4B angled off from the feed part 4A. In this embodiment variant, the light projector 41 comprises a first lens system 43 in the projection part 4B and a second lens system 42 in the feed part 4A. The first lens system 43 and the second lens system 42 are coupled via the deflecting mirror 45. The application head 4 preferably also has a viewing window 44 permitting a top view of the eye 6 in the projection direction v. The viewing window 44 is designed, for example, such that the deflecting mirror 45 is transparent to light for the viewing wavelength. Reference number 47 designates coupling means, which are described in more detail below.

Figure 8:
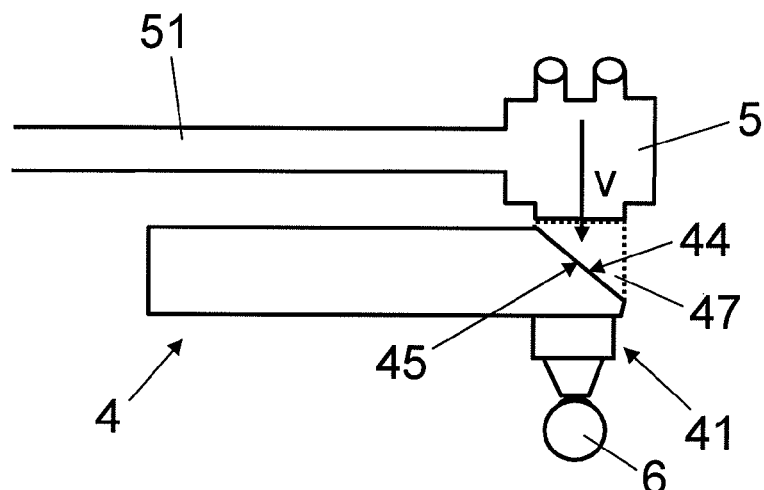
FIG. 8 shows a schematic side view of the application head, comprising a viewing window over the projection part, to which an optical viewing aid or measuring module is coupled in a releasable manner.

As is shown schematically in FIG. 8, the viewing window 44 permits optical coupling of optical viewing, imaging and measuring modules 5, e.g. a recording camera with optional pivotable monitor, which are mounted, for example by way of a module support 51, on the base station 2 so as to rotate about a vertically oriented rotation axis. These modules can thus be swivelled in and out over the application head 4, and their optical axes can be oriented with respect to the optical projection axis v of the light projector 41. The modules can additionally be mechanically connected to the application head 4 in a releasable manner via the coupling means 47, for example a detachable snap-fit catch or a bayonet catch.

Figure 9:
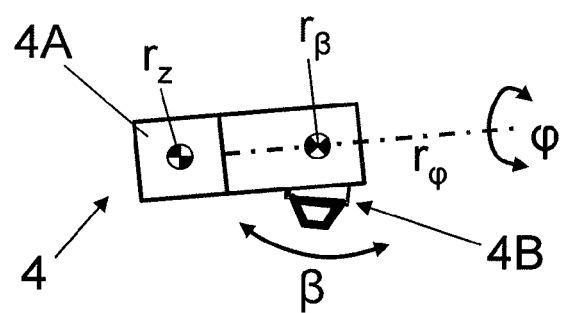
FIGS. 9 and 9a show a schematic side view of the application head, comprising a projection part connected rotatably to the feed part.

In an optional embodiment variant that can be combined with FIGS. 1-8 and is shown schematically in FIG. 9, the projection part 4B is mounted pivotably on the feed part 4A. In the variant according to FIG. 9, the application head 4 has a hinge RΦ and the projection part 4B is rotatably connected with the angle p about a longitudinal axis $r_\Phi$ extending through the feed part 4A. The application head 4 additionally has a hinge $R_\beta$ and the projection part 4B is rotatably connected to the feed part 4A with the angle β about a transverse axis $r_\beta$ extending perpendicular to the longitudinal axis $r_\Phi$.

Figure 9A:
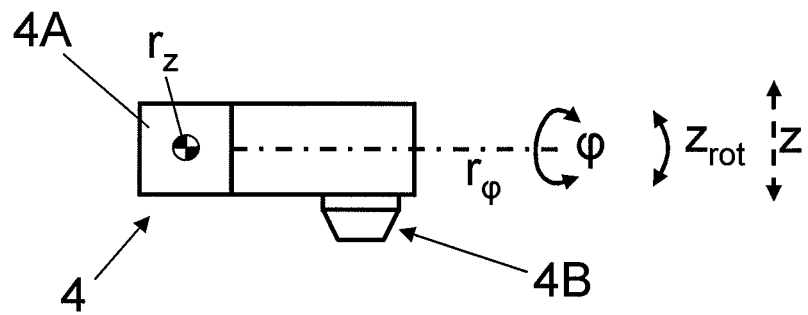
Figure 9B:
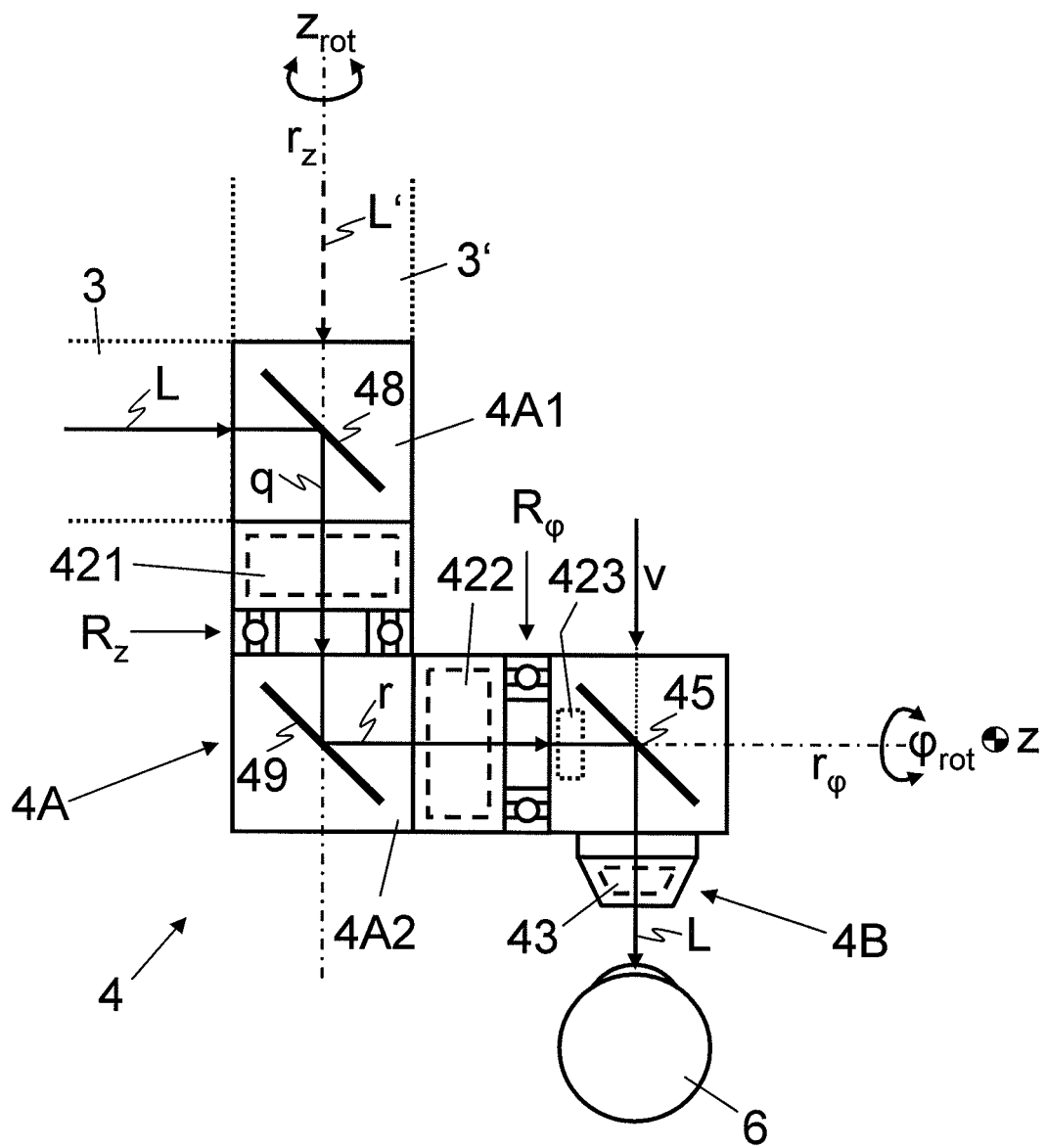
FIG. 9b shows the application head with a schematic top view of its feed system, the application head comprising one lens system in the feed system and another lens system in the projection part which is connected rotatably to the feed system.

FIGS. 9a and 9b show an embodiment variant of the application head 4 shown in FIG. 9 without the hinge $R_\beta$, which embodiment variant can be combined with FIGS. 1-8.

As described above in the context of FIG. 7, the application head 4 has a feeding system 4A connected to the support arm 3, and a projection part 4B angled off from the feeding system 4A.

As described above in the context of FIGS. 1 to 6, the application head 4 is connected to the support arm 3 via the hinge $R_z$ so as to make possible a rotation $z_{rot}$ of the application head 4 about the (constantly) horizontally oriented rotation axis $r_z$.

As described above in the context of FIGS. 1 and 2, and as indicated in FIG. 9a, the rotation $z_{rot}$ of the application head 4, with its feeding system 4A and projection part 4B, about the horizontal rotation axis $r_z$ makes it possible to execute a vertical movement component in z-direction for lowering and placing the application head 4, particularly its projection part 4B, onto an eye 6.

As described above with reference to FIG. 9, in an embodiment, the projection part 4B is mounted pivotably on the feeding system 4A. Specifically, as shown in FIG. 9b, in this embodiment, the projection part 4B is connected to the feeding system 4A through hinge $R_\Phi$ which makes it possible to execute a rotation $\Phi_{rot}$ of the projection part 4B about the rotation axis $r_\Phi$. The rotation axis $r_\Phi$ of the hinge $R_\Phi$ runs at a fixed angle with respect to the rotation axis $r_z$ of the horizontally oriented hinge $R_z$, e.g. normal) (90°) and, thus, making it possible to rotate the projection part 4B in a plane parallel to the horizontal rotation axis $r_z$. Nevertheless, it should be noted that the pivotable mounting of the projection part 4B on the feeding system 4A is optional.

FIG. 9b shows the feeding system 4A in top view, while the projection part 4B is shown in a state where the projection direction v of the projection part 4B runs parallel to the horizontal rotation axis $r_z$ of the feeding system 4a, as a result of having rotated the projection part 4B about the rotation axis $r_\Phi$. As is illustrated in FIG. 9b, the feeding system 4A comprises a first feed part 4A1 which is connected to the support arm 3, and a second feed part 4A2 which is arranged downstream from the first feed part 4A1 and connected to the projection part 4B. The first feed part 4A1 and the second feed part 4A2 are connected through the horizontally oriented hinge $R_z$. The horizontally oriented hinge $R_z$ makes it possible to rotate the second feed part 4A2 about the horizontal rotation axis $r_z$. The projection part 4B is arranged downstream from the second feed part 4A2. The second feed part 4A2 and the projection part 4B are connected through hinge $R_\Phi$.

As described above with reference to FIG. 7, a first lens system 43 is arranged in the projection part 4B and a second lens system 42 is arranged in the feeding system 4A. The first lens system 43 and the second lens system 42 are coupled optically via the deflecting mirror 45 arranged in a fixed fashion in the projection part 4B. As illustrated in FIG. 9b, a first part 421 of the second lens system 42 is arranged in the first feed part 4A1 and a second part 422 of the second lens system 42 is arranged in the second feed part 4A2. The first part 421 of the second lens system 42 and the second part 422 of the second lens system 42 are coupled optically via the deflecting mirror 49.

The application head 4 is coupled optically to the optical transmission system 22 via the deflecting mirror 48 arranged in a fixed fashion in the first feed part 4A1.

The second feed part 4A2 is coupled optically to the first feed part 4A1 via the deflecting mirror 49 arranged in a fixed fashion in the second feed part 4A2.

As illustrated in FIG. 9b, the laser pulses L (femtosecond laser pulses), received from the laser source 21 via the optical transmission system 22, are guided in the application head 4 along an optical path q from the deflecting mirror 48 arranged in the first feed part 4A1, through the first part 421 of the second lens system 42, to the deflecting mirror 49 arranged in the second feed part 4A2. As shown in FIG. 9b, the optical path q, through the first part 421 of the second lens system 42, coincides with the horizontal rotation axis $r_z$ of the hinge $R_z$ interconnecting the first feed part 4A1 and the second feed part 4A2. In an alternative embodiment, indicated in FIG. 9b by reference numerals L', 3', the support arm 3' is aligned with the first feed part 4A1 such that the laser pulses L' are received from the laser source 21 via the optical transmission system 22 along an optical axis, which coincides with the optical path q and the horizontal rotation axis $r_z$, so that there is no need for the deflecting mirror 48.

Further downstream, the laser pulses L are guided in the application head 4 along an optical path r from the deflecting mirror 49 arranged in the second feed part 4A2, through the second part 422 of the second lens system 42, to the deflecting mirror 45 arranged in the projection part 4B. As shown in FIG. 9b, the optical path r, through the second part 422 of the second lens system 42, coincides with the rotation axis $r_\Phi$ of the hinge $R_\Phi$ interconnecting the second feed part 4A2 and the projection part 4B.

The first part 421 of the second lens system 42 and the second part 422 of the second lens system 42 are rotationally symmetrical with respect to the rotation axis $r_z$ or the rotation axis $r_\Phi$, respectively. The second lens system 42 (including the first and second parts 421, 422 of the lens system 42), is configured to compensate optical aberrations of the optical transmission system 22 and/or the first lens system 41 arranged in the projection part 4B. One skilled in the art will understand that, in different embodiments, the first part 421 of the second lens system 42 and/or the second part 422 of the second lens system 42 can be arranged upstream, as illustrated in FIG. 9b, or downstream from hinge $R_z$ or $R_\Phi$, respectively. Moreover, in further embodiments, an third part 423 of the second lens system 42 is arranged downstream from hinge $R_\Phi$, in addition to the first and second parts 421, 422, as indicated in FIG. 9b; or one or two of the first, second, and third parts 421, 422, 423 are eliminated from the second lens system 42.

In an embodiment, the second lens system 42 is configured to compensate actively and dynamically the optical aberrations of the optical transmission system 22 and/or the first lens system 41. Specifically, the first, second and/or third parts 421, 422, 423 of the second lens system 42, are provided with one or more movement drivers (e.g. electrical motors) to move one or more individual lenses of the second lens system 42 along the optical path q, r of the feeding system 4A to adjust the focus of the laser pulses L in projection direction v and/or to compensate actively and dynamically the optical aberrations. The active compensation of the optical aberrations is controlled by a control module using a feedback signal indicative of aberration errors.

To reduce optical aberrations created by alignment errors of the optical axes, specifically the optical paths q and r, with the rotation axes, specifically the rotation axis $r_z$ and $r_\Phi$, the hinges $R_z$, $R_\Phi$, and the parts 421, 422, 423 of the second lens system 42 are configured and arranged such that reciprocal rotation is enabled only for those pairs of parts 421, 422, 423 of the second lens system 42 that form in between the two respective parts 421, 422, 423 an intermediate focal plane or an essentially collimated laser beam.

In the embodiment variant according to FIG. 1, the support arm 3 is fixedly connected to the base station 2, for example the base station 2 and the support arm 3 are designed in one piece as an overall unit with a common housing. In this variant, the mutual orientation of eye 6 and light projector 41, i.e. the centring of the light projector 41 to the eye 6, is effected by moving the patient's bed or the base station 2 in the x-direction and y-direction of a horizontal positioning plane (generally parallel to the ground surface on which the base station 2 is arranged).

Figure 2:
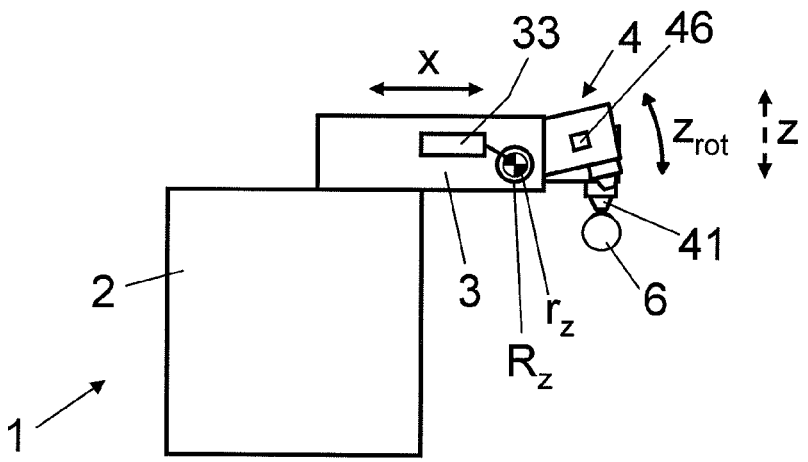
FIG. 2 shows a schematic side view of an ophthalmological apparatus comprising a support arm which can be moved in translation relative to the base station in a horizontal positioning plane and on which the application head is mounted rotatably.
Figure 3:
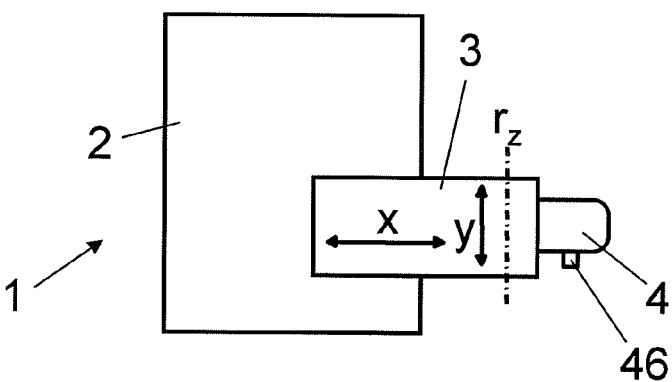
FIG. 3 shows a schematic top view of an ophthalmological apparatus comprising a support arm which can be moved in translation relative to the base station in the positioning plane and on which the application head is mounted rotatably.

In the embodiment variant according to FIGS. 2 and 3, the support arm 3 is connected movably to the base station 2 such that the support arm 3, for orientation of the light projector 41 to the eye 6, can be moved in translation in the x-direction and y-direction of a horizontal positioning plane relative to the base station 2. The translatory movement is effected by means of translatory movement drivers or manually via corresponding guides.

Figure 4:
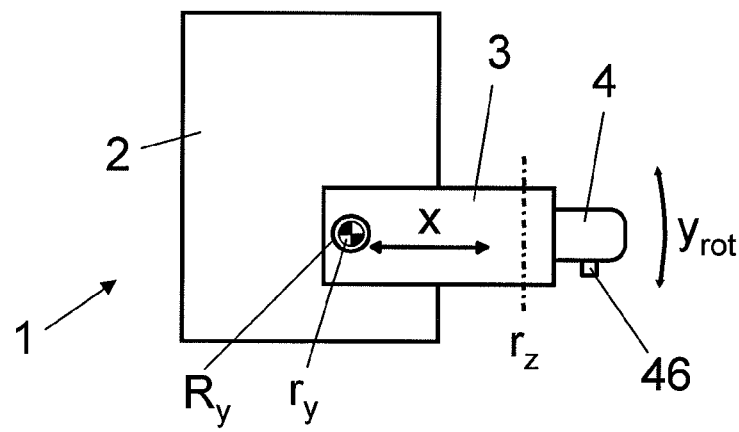
FIG. 4 shows a schematic top view of an ophthalmological apparatus comprising a support arm which can be moved in translation and rotation relative to the base station in the positioning plane and on which the application head is mounted rotatably.

In the embodiment variant according to FIG. 4, the support arm 3 is connected to the base station 2 via the hinge Ry. The hinge Ry permits a rotation $y_{rot}$ of the support arm 3 about the vertical rotation axis $r_y$. As is shown schematically in FIG. 4, the hinge $R_y$ is arranged and configured such that, by the rotation $y_{rot}$ of the support arm 3 about the rotation axis $r_y$, a horizontal movement is permitted in the y-direction for orienting the light projector 41 to the eye 6. The orientation of the light projector 41 in the x-direction is effected by means of translatory movement, as in FIGS. 2 and 3.

In the embodiment variant according to FIG. 5, the orientation of the light projector 41 is effected by rotation both in the x-direction and also in the y-direction. In the embodiment variant according to FIG. 4, the application head 4 is connected to that end of the support arm 3 directed away from the base station 2, in particular also via the hinge $R_x$. The hinge $R_x$ permits a rotation $x_{rot}$ of the application head 4 about the vertical axis $r_x$. As is shown schematically in FIG. 5, the hinge $R_x$ is arranged and configured such that, by the rotation $x_{rot}$ of the application head 4 about the rotation axis $r_x$, a horizontal movement in the x-direction is permitted for orienting the light projector 41 to the eye 6. The orientation of the light projector 41 in the y-direction is effected by means of a rotary movement, as in FIG. 4.

In the embodiment variant according to FIG. 6, the orientation of the light projector 41 is effected by rotation both in the x-direction and also in the y-direction, as in FIG. 5. In the embodiment variant according to FIG. 6, however, the hinge $R_z$ or rotation axis $r_z$ is turned through 90° in relation to the arrangement according to FIG. 5. The movement in the x-direction is effected by a rotation $x_{rot}$ of the support arm 3 about the vertical rotation axis $r_x$ of the hinge $R_x$, which connects the support arm 3 to the base station 2. The movement in the y-direction is effected by a rotation $y_{rot}$ of the application head 4 about the vertical axis $r_y$ of the hinge $R_y$, which connects the application head 4 to the support arm 3.

The positioning means for the rotatory and/or translatory movement of the support arm 3 for horizontal orientation of the application head 4 and of the light projector 41 with translatory movements in the x-direction and y-direction and/or with rotary movements $x_{rot}$ and $y_{rot}$ can be configured for manual movement and/or by means of movement drivers.

Although this is only shown schematically in FIG. 2, the ophthalmological apparatus 1 comprises weight compensation means 33 which are connected to the application head 4, for example adjustable counter-weights or springs. The weight compensation means 33 are preferably configured such that they only partially balance out the masses rotating about the rotation axis $r_z$, such that the application head 4 can be placed with a defined application force onto the eye 6.

Although the figures and the above observations only concern embodiment variants in which the application head 4 for carrying out the vertical orientation in the z-direction is connected to the support arm 3 via the hinge $R_z$, it should be noted here that the vertical orientation of the application head 4 in the z-direction can also be effected via a rotation movement of the support arm 3 about a horizontal rotation axis $r_z$, if the support arm 3 is connected via a corresponding hinge $R_z$ to the base station 2, and the application head 4 is mounted fixedly on the support arm 3. The horizontal orientation of the application head 4 or light projector 41 with translatory movements in the x-direction and y-direction and/or with rotary rotations $x_{rot}$ and $y_{rot}$ also takes place through the positioning means for the rotary and/or translatory movement of the support arm 3 in accordance with the above description. Depending on the arrangement of the positioning means for the rotary and/or translatory movement of the support arm 3, the hinge $R_z$ remains fixedly connected to the base station or moved along with it.

Although this is only shown schematically in FIG. 1, the ophthalmological apparatus 1 additionally comprises a control unit 23 arranged in the base station 2. The control unit 23 ensures that the beam-deflecting means 31 are not activated when the application head 4 is moved for placement onto the eye 6. The control unit 23 is also designed for controlling the beam deflection and for controlling and monitoring the movement drivers. The control unit 23 additionally comprises safety functions for monitoring of forces, movements and beam parameters.

In one embodiment variant, the ophthalmological apparatus 1 moreover comprises height-defining means 22 for determining a vertical position of the eye 6, for example a camera, and the base station 2 comprises height-positioning means 24, e.g. translatory movement drivers, for setting a vertical basic position of the base station 2 and of the associated support arm 3. The height-positioning means 24 are controlled, for example, by the control unit 23 on the basis of a vertical position of the eye 6 determined by the height-defining means 22. Manual setting of the basic position is also possible. By setting the basic position, the movement stroke required for the application head 4 can be reduced to 10-20 mm, for example.

What is claimed is:
1. An ophthalmological apparatus, comprising:
   a base station with a light source configured to generate light pulses;
   an application head connected to the base station; and an optical transmission system configured to transmit the light pulses from the base station to the application head;

the application head comprising:

a projection part configured for focused projection of the light pulses for punctiform breakdown of eye tissue, and a feeding system configured to transmit the light pulses from the optical transmission system along an optical path to the projection part, the feeding system residing in an application head housing that is independent from the base station;

wherein the feeding system is connected to the base station via a first hinge, having a first rotation axis with a horizontal orientation, for placing the application head onto an eye with a rotation extending about the first rotation axis, the first rotation axis coinciding with the optical path of the feeding system.

2. The ophthalmological apparatus of claim 1, wherein the feeding system comprises a lens system configured to compensate optical aberrations of at least one of: the optical transmission system and the projection part.

3. The ophthalmological apparatus of claim 1, wherein the projection part is connected to the feeding system via a second hinge having a second rotation axis arranged at an angle to the first rotation axis, the second rotation axis coinciding with the optical path of the feeding system.

4. The ophthalmological apparatus of claim 3, wherein the feeding system comprises a lens system configured to compensate optical aberrations of at least one of: the optical transmission system and the projection part.

5. The ophthalmological apparatus of claim 4, wherein the lens system comprises a first part having a first optical path which coincides with the first rotation axis, and a second part having a second optical path which coincides with the second rotation axis.

6. The ophthalmological apparatus of claim 4, wherein the lens system comprises a first part configured rotationally symmetrical with respect to the first rotation axis, and a second part configured rotationally symmetrical with respect to the second rotation axis.

7. The ophthalmological apparatus of claim 4, wherein the feeding system comprises a first feed part and a second feed part which are connected via the first hinge; and the lens system comprises a first part arranged in the first feed part and a second part arranged in the second feed part.

8. The ophthalmological apparatus of claim 7, wherein the first feed part is connected to the base station, and the projection part is connected to the second feed part via the second hinge.

9. The ophthalmological apparatus of claim 7, wherein the application head is coupled optically to the optical transmission system via a first deflecting mirror arranged in a fixed fashion in the first feed part; the second feed part is coupled optically to the first feed part via a second deflecting mirror arranged in a fixed fashion in the second feed part; and the projection part is coupled optically to the second feed part via a third deflecting mirror arranged in a fixed fashion in the projection part.

10. The ophthalmological apparatus of claim 3, wherein the second rotation axis is arranged normal to the first rotation axis.

11. The ophthalmological apparatus of claim 1, wherein the application head has a viewing window permitting a top view onto the eye in projection direction of the light projector.

12. The ophthalmological apparatus of claim 1, wherein the application head comprises a contact body which can be placed onto the eye, is transparent to light at least in parts and is configured and arranged such that it sets a contacted area of the eye equidistant to a work surface; the application head has securing means for fixing the application head on the eye by underpressure; and the light source comprises a femtosecond laser.

13. The ophthalmological apparatus of claim 1, further comprising a support arm mounted on the base station; the application head being mounted on the support arm; and the optical transmission system being configured to transmit the light pulses from the base station through the support arm to the application head.

* * * * *